(12) United States Patent
Chauhan et al.

(10) Patent No.: US 12,310,724 B2
(45) Date of Patent: May 27, 2025

(54) CLOUD-BASED PORTABLE SYSTEM FOR NON-INVASIVE REAL-TIME BLOOD GLUCOSE MEASUREMENT

(71) Applicant: Analog Devices, Inc., Wilmington, MA (US)

(72) Inventors: Hari Chauhan, Revere, MA (US); J. Brian Harrington, Revere, MA (US); Teoman Emre Ustun, Lexington, MA (US); Alexander Gray, Andover, MA (US)

(73) Assignee: ANALOG DEVICES, INC., Wilmington, MA (US)

( * ) Notice: Subject to any disclaimer, the term of this patent is extended or adjusted under 35 U.S.C. 154(b) by 903 days.

(21) Appl. No.: 17/347,163

(22) Filed: Jun. 14, 2021

(65) Prior Publication Data
US 2021/0307660 A1    Oct. 7, 2021

Related U.S. Application Data

(63) Continuation of application No. PCT/US2019/064200, filed on Dec. 3, 2019.
(Continued)

(51) Int. Cl.
*A61B 5/1455*    (2006.01)
*A61B 5/00*      (2006.01)
(Continued)

(52) U.S. Cl.
CPC ........ *A61B 5/14532* (2013.01); *A61B 5/0004* (2013.01); *A61B 5/0075* (2013.01);
(Continued)

(58) Field of Classification Search
CPC ..... A61B 5/0004; A61B 5/0075; A61B 5/082; A61B 5/083; A61B 5/091; A61B 5/097;
(Continued)

(56) References Cited

U.S. PATENT DOCUMENTS 5,638,816 A * 6/1997 Kiani-Azarbayjany ..................... A61B 5/6826
600/316
8,991,238 B2  3/2015 Lee et al.
(Continued)

FOREIGN PATENT DOCUMENTS

KR   20180043832   4/2018
WO   2018141752    8/2018

OTHER PUBLICATIONS

Saasa et al., *Sensing Technologies for Detection of Acetone in Human Breath for Diabetes Diagnosis and Monitoring*, diagnostics, Jan. 31, 2018, 17 pages.
(Continued)

*Primary Examiner* — Chu Chuan Liu
(74) *Attorney, Agent, or Firm* — ARENTFOX SCHIFF LLP (57) ABSTRACT

One embodiment is a method for implementing a cloud-based portable miniaturized system for performing non-invasive blood glucose level measurement in real time. The method includes using an optical source to emit optical radiations at certain wavelengths through breath in an air collection chamber; receiving the emitted optical transmissions at a photodetector; converting the received optical transmissions to digital data; accumulating the digital data for a first time period; and periodically transmitting the accumulated digital data to a cloud service for further processing.

4 Claims, 7 Drawing Sheets

Related U.S. Application Data (60) Provisional application No. 62/781,491, filed on Dec. 18, 2018.

(51) Int. Cl.
    *A61B 5/08*         (2006.01)
    *A61B 5/097*       (2006.01)
    *A61B 5/145*       (2006.01)

(52) U.S. Cl.
    CPC .............. *A61B 5/082* (2013.01); *A61B 5/097* (2013.01); *A61B 5/1455* (2013.01); *A61B 2562/0271* (2013.01)

(58) Field of Classification Search
    CPC .............. A61B 5/1455; A61B 5/14551; A61B 5/14552; A61B 5/14532; A61B 5/14546
    See application file for complete search history.

(56) References Cited

U.S. PATENT DOCUMENTS

| | | |
|---|---|---|
| 2002/0026937 A1 | 3/2002 | Mault |
| 2002/0123677 A1 | 9/2002 | Miki et al. |
| 2003/0208133 A1* | 11/2003 | Mault ............... A61B 5/087 600/531 |
| 2004/0236244 A1 | 11/2004 | Allen et al. |
| 2007/0203448 A1 | 8/2007 | Melker et al. |
| 2008/0159341 A1 | 7/2008 | Patel et al. |
| 2009/0155770 A1 | 6/2009 | Brown et al. |
| 2011/0102788 A1 | 5/2011 | Patel et al. |
| 2011/0103411 A1 | 5/2011 | Patel et al. |
| 2011/0103412 A1 | 5/2011 | Patel et al. |
| 2011/0103416 A1 | 5/2011 | Patel et al. |
| 2011/0158270 A1 | 6/2011 | Patel et al. |
| 2014/0303463 A1 | 10/2014 | Robinson et al. |
| 2015/0177224 A1* | 6/2015 | Priefer ............... A61B 5/097 436/130 |
| 2015/0289782 A1 | 10/2015 | Peverall et al. |
| 2016/0051169 A1 | 2/2016 | Hong et al. |
| 2017/0224251 A1 | 8/2017 | Ahmad et al. |
| 2017/0224261 A1 | 8/2017 | Sarrafzadeh et al. |
| 2017/0227455 A1 | 8/2017 | Kakuno et al. |
| 2017/0367636 A1 | 12/2017 | Mantinband et al. |
| 2018/0055488 A1 | 3/2018 | Hall et al. |
| 2018/0271404 A1 | 9/2018 | Gupta et al. |
| 2021/0311018 A1 | 10/2021 | Harrington et al. |

OTHER PUBLICATIONS

Bruen et al., *Glucose Sensing for Diabetes Monitoring: Recent Developments*, sensors, Aug. 12, 2017, 21 pages.

Walton et al., *The Use of a Portable Breath Analysis Device in Monitoring Type 1 Diabetes Patients in a Hypoglycaemic Clamp: Validation with SIFT-MS Data*, The Open University, © 2014, 20 pages.

Priefer et al., *Pain-Free Diabetic Glucose Breath Detector*, GLUCAIR™ Diabetic Monitor © 2016, 3 pages.

Righettoni et al., *Breath Analysis by Nanostructured Metal Oxides as Chemo-Resistive Gas Sensors*, Materials Today, vol. 18, No. 3, Apr. 2015, 9 pages.

*Handheld Breathalyzer as Noninvasive Blood Glucose Monitor in Development*, www.drugdeliverybusiness.com/handheld-breathalyzer-noninvasive-blood-glucose...10-22-2019, 5 pages.

Bayer et al., *Potential and Challenges for Mid-Infrared Sensors in Breath Diagnostics*, IEEE Sensors Journal, Feb. 2010, 15 pages.

Martinez et al., *Room Temperature Detection of Acetone by a PANI/Cellulose/WO3 Electrochemical Sensor*, Journal of Nanomaterials, vol. 2018, Article ID 6519694, 10 pages.

Holthoff et al., *Quantum Cascade Laser-Based Photoacoustic Spectroscopy for Trace Vapor Detection and Molecular Discrimination*, sensors 2010, 10, 17 pages.

Kao et al., *A Sub-ppm Acetone Gas Sensor for Diabetes Detection Using 10 nm Thick Ultrathin InN FETs*, sensors, 2012, 12, 12 pages. https://image.slidesharecdn.com/gc-osniffer-130523082619-phpapp01/95/gas-chromatography-olfactometry-sniffer-4-638.jpg?cb=1490625887, 1 page.

Wang et al., *Is Breath Acetone a Biomarker of Diabetes? A Historical Review on Breath Acetone Measurements*, Aug. 20, 2013 IOPScience, 4 pages. http://iopscience.iop.org/article/10.1088/1752-7155/7/3/037109.

Li et al., *A Cross-Sectional Study of Breath Acetone Based on Diabetic Metabolic Disorders*, Feb. 26, 2015, IOPScience, 4 pages. http://iopscience.iop.org/article/10.1088/1752-7155/9/1/016005.

International Search Report and Written Opinion issued in PCT Application No. PCT/US2019/06416 mailed May 15, 2020, 14 pages.

International Search Report and Written Opinion issued in PCT Application No. PCT/US2019/064200 mailed Jul. 3, 2020, 10 pages.

Andor, "An introduction to Absorption / Transmission / Reflection Spectroscopy", Jan. 17, 2017, Photonics Spectra, chrome-extension://efaidnbmnnnibpcajpcglclefindmkaj/https://www.photonics.com/images/Web/WhitePapers/532/Andor_Learning_Absorption_Transmission_Reflection_Spectroscopy_For_Photonics.pdf, 4 pages.

Bijlsma et al., "Simultaneous ultra-high-pressure liquid chromatography-tandem mass spectrometry determination of amphetamine and amphetamine-like stimulants, cocaine and its metabolites, and a cannabis metabolite in surface water and urban wastewater", Jan. 29, 2009, Journal of Chromatography A, vol. 1216, No. 15, 12 pages.

Curròet al., "Technical Note: Feasibility of near infrared transmittance spectroscopy to predict cheese ripeness", 2017, Journal of Dairy Science, vol. 100, No. 11, 5 pages.

Fitzgerald et al., "The Internet of Things (IoT) for a Smartphone-enabled Optical Spectrometer and its use On-site and (potentially) for Industry 4.0", 2018, Next-Generation Spectroscopic Technologies XI, Proc. of SPIE, vol. 10657, 11 pages.

Huang et al., Urinalysis with molecularly imprinted poly(ethylene-co-vinyl alcohol) potentiostats sensors, Feb. 2009, Biosensors and Bioelectronics, vol. 24, https://www.researchgate.net/pubcation/24028502_urinalysis_with_molecularly_imprinted_polyethylene-co-vinyl_alcohol_potentiostats_sensors, 7 pages.

Ince et al., "The comparison of automated urine analyzers with manual microscopic examination for urinalysis automated urine analyzers and manual urinalysis", Mar. 11, 2016, Practical Laboratory Medicine, vol. 5, 7 pages.

Ioller et al., "Development of an Automatic Urine Monitoring Devices Using Cross-Selectivity Sensing Principle", 2018, 2018 International Conference on Electronics Packaging and iMAPS All Asia Conference (ICEP-IAAC), https://ieeexplore.IEEE.org/stamp/stamp.isp?tp=&arnumber=8374315, 4 pages.

Maleki et al., "Multiplicative Scatter Correction during On-line Measurement with Near Infrared Spectroscopy", 2007, Biosystems Engineering, vol. 96, No. 3, 7 pages.

Ra et al., "Smartphone-Based Point-of-Care Urinalysis Under Variable Illumination", Dec. 15, 2017, IEEE Journal of Translational Engineering in Health and Medicine, 11 pages.

Simerville et al., "Urinalysis: A Comprehensive Review", Mar. 15, 2005, American Family Physician, vol. 71, No. 6, 10 pages.

"Urinalysis", Apr. 21, 2021, Lab Tests Online, https://labtestsonline.org/tests/urinalysis, 21 pages.

Yu et al., "Label Free Detection of Sensitive Mid-Infrared Biomarkers of Glomerulonephritis in Urine Using Fourier Transform Infrared Spectroscopy", Jul. 4, 2017, Scientific Reports, vol. 7, No. 4601, 12 pages.

\* cited by examiner

CLOUD-BASED PORTABLE SYSTEM FOR NON-INVASIVE REAL-TIME BLOOD GLUCOSE MEASUREMENT

CROSS-REFERENCE TO RELATED APPLICATIONS

This application claims the benefit of and priority to U.S. Patent Application Ser. No. 62/781,491, filed Dec. 18, 2018, entitled "CLOUD-BASED PORTABLE SYSTEM FOR NON-INVASIVE REAL-TIME BLOOD GLUCOSE MEASUREMENT," and PCT Patent Application No. PCT/US2019/064200, filed Dec. 3, 2019, entitled "CLOUD-BASED PORTABLE SYSTEM FOR NON-INVASIVE REAL-TIME BLOOD GLUCOSE MEASUREMENT", each of which is incorporated herein by reference in its entirety.

FIELD OF THE DISCLOSURE

This disclosure relates generally to the field of blood glucose analysis systems and, more particularly, to a cloud-based portable miniaturized system for performing non-invasive blood glucose measurement in real time.

BACKGROUND

A variety of tests exists for estimating blood glucose levels at a particular point in time or over a period of time to determine average levels or to determine how fast a body is able to normalize changed levels. For example, in a healthy person, elevated blood glucose (or sugar) levels caused by eating return quickly to a normal level via increased cellular glucose uptake, which is primarily mediated by an increase in blood insulin levels. Blood glucose tests can reveal temporary or long-term high blood sugar (hyperglycemia) or low blood sugar (hypoglycemia), either of which may not present obvious symptoms but may damage organs overtime. Abnormal blood sugar levels (high or low), slow return to normal levels from either high or low levels, or inability to normalize blood sugar levels may indicate the existence of a medical condition, such as type 2 diabetes, that should be treated. Accordingly, blood glucose tests are often used to diagnose such conditions.

SUMMARY OF THE DISCLOSURE

One embodiment is a method for implementing a cloud-based portable miniaturized system for performing non-invasive blood glucose level measurement in real time. The method includes using an optical source to emit optical radiations at certain wavelengths through breath in an air collection chamber; receiving the emitted optical transmissions at a photodetector; converting the received optical transmissions to digital data; accumulating the digital data for a first time period; and periodically transmitting the accumulated digital data to a cloud service for further processing. Some embodiments may also include an electrochemical sensor and readout system that would generate digital data that would be combined with the accumulated optical data prior to being transmitted to the cloud services.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Embodiments described herein comprise a cloud-based system for performing real time measurement of small hydrocarbon molecules in air. Some embodiments comprise a cloud-based system that indirectly measures blood glucose levels using a correlation between acetone levels in exhaled breath and blood glucose levels. Embodiments may include a spectroscopic method for measuring exhaled acetone levels and computational algorithms for correlating the measured acetone levels to blood glucose levels. Other applications may include a spectroscopic method for measuring ethylene levels in sampled air and computational algorithms for correlating the measured ethylene levels to the ripeness level of fruits.

Embodiments described herein comprise a complete cloud-connected system that includes an air chamber, a spectrometric system, and cloud services infrastructure. In certain embodiments, the spectrometric system includes a source, which may be implemented using a Quantum Cascade Laser ("QCL"), and a detector. In some embodiments, the QCL functionality may be replaced by an ADSC100, available from Analog Devices of Norwood, Mass., which is a miniaturized near infrared ("NIR") spectrometer. The ADSC100 contains a broadband NIR light source, optical filters and detectors comprising a miniaturized NIR spectrometer. The QCL function may alternatively be replaced by a plurality of discrete LEDs.

Figure 1A:
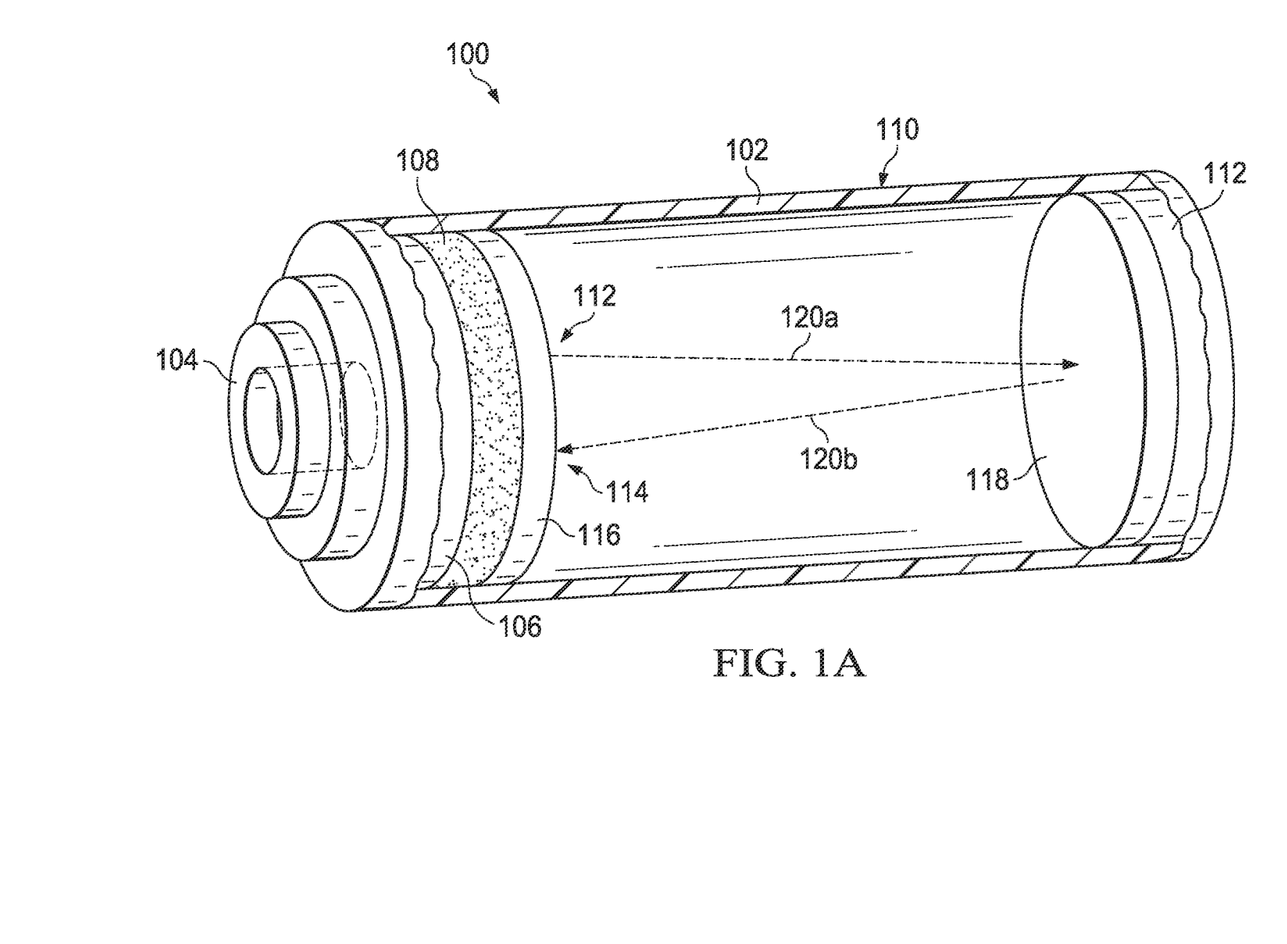
FIG. 1A illustrates a cloud-based portable miniaturized system for non-invasive real-time blood glucose analysis in accordance with embodiments described herein.

FIG. 1A is a perspective illustration of a cloud-based portable handheld system 100 for non-invasive real-time blood glucose monitoring in accordance with embodiments described herein. As shown in FIG. 1A, the system 100 includes an air chamber 102 that is used to collect breath exhaled by a patient. The air chamber 102 includes an air inlet mechanism 104, an air inlet diaphragm 106, a particulate filter 108, an air containment tube 110, and an air outlet diaphragm 112. A purpose of the chamber 102 is to precondition the breath for measurement by removing water vapor and other larger particulate matter that could interfere with the spectroscopic measurement. The filter 108 acts to reduce the amount of required cleaning of the chamber. In operation, the air to be analyzed enters through the air inlet mechanism 104 of the chamber 102. The air inlet mechanism could be a mouthpiece through which a patient exhales, or a micropump which samples ambient air. The exhaled breath (or sampled air) passes through the filter 108 and inlet diaphragm 106, forcing existing air in the air containment tube 110 out through the outlet diaphragm 112, effectively exchanging the air in the tube 110 with the newly acquired gas sample. In certain embodiments, the air containment tube 110 may be equipped with humidity and temperature sensors to record the precise measurement conditions. For purposes that will be described in greater detail below, the interior walls of the air containment tube 110 may be equipped with small reflective surfaces (such as mirrors) or coated with a reflective coating for reflecting the optical radiations, thus enabling the long-path length optical measurements desired for measuring smaller concentrations of analytes from the air samples inside the tube 110. In addition, as will be described in detail below with reference to FIG. 1B, the air chamber 102 may be equipped with the required electronic system to transmit the measurement conditions and the measured spectrum of the exhaled breath to the cloud. In particular, a source 112 and a detector 114 (e.g., an infrared ("IR") detector) may be provided within the chamber 102 (e.g., disposed on a surface of a spectrometer/sensor printed circuit board ('PCB') 116) such that radiation emitted from the source travels to the detector (e.g., via a reflective surfaces within the tube 110, such as reflective/diffusive surface 118) through the breath, as represented by arrows 120a, 120b. The reflective surface(s) and the configurable detector position enables adjustment of optical path length for better sensitivity. As an example, the detector position with respect to the source (which may be QCL or NIR/IR) along the optical path provides flexibility to increase or decrease the optical path length as needed by increasing/decreasing the number of transmissions/reflections between the transmitter and receiver.

Figure 1B:
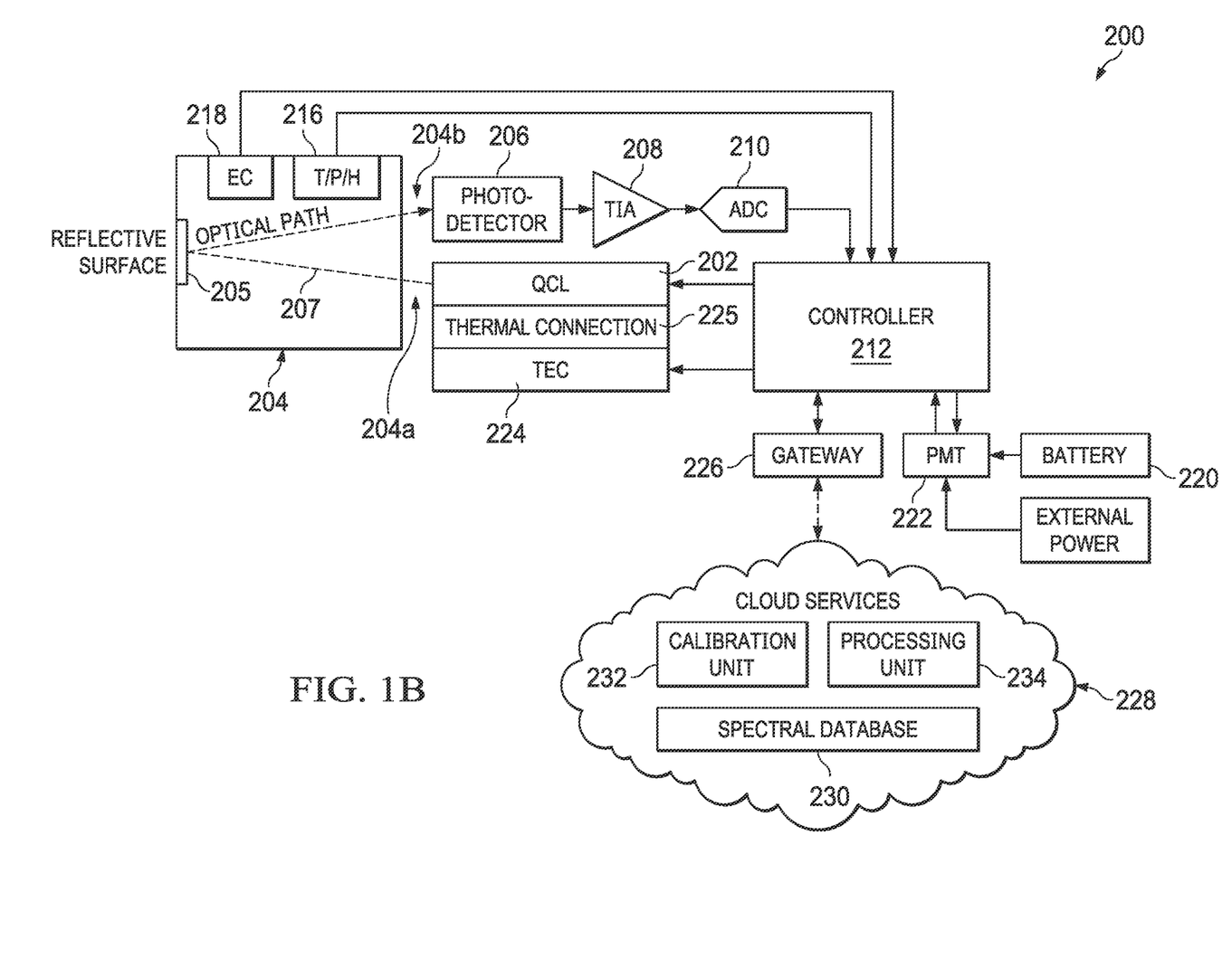
FIG. 1B is a schematic block diagram of a cloud-based portable miniaturized system for non-invasive real-time blood glucose analysis in accordance with embodiments described herein.

As previously noted, in one embodiment, as will be described in greater detail below, the source 112 is implemented using a QCL (and/or miniaturized NIR/IR spectrometer, such as such the aforementioned ADSC100, or discrete LEDs and detector combinations), which emits radiation having a predetermined wavelength. The inner surfaces of the reflective arm 104 and the base arm 102 are coated with IR reflective material or IR reflective mirrors to allow the emitted radiation to experience multiple reflections through the gas sample before reaching the detector. In certain embodiments, the system housing is equipped with a temperature sensor and/or humidity sensor to measure temperature/humidity of the gas sample. Alternatively, the IR radiation can also be used to measure the temperature of the gas sample. As shown in FIG. 1B, the system 100 is also equipped with the electronics necessary to convert the received light into digital data, calculate the raw spectral power density (spectrum) and to transmit the measured temperature and the spectrum of the breath sample to the cloud.

Referring now to FIG. 1B, illustrated therein is a system block diagram of a spectrometer system 200 for use in implementing a cloud-based portable handheld system, such as system 100, for non-invasive real-time blood glucose analysis in accordance with embodiments described herein. In the illustrated embodiment, the system 200 comprises a chip-scale QCL-based spectrometer system. The spectrometer system 200 operates by measuring the optical transmission of the laser beam through the breath/gas captured in the air chamber. As shown in FIG. 1B, the spectrometer system 200 includes a chip-scale QCL source 202 that transmits highly focused optical radiations at certain wavelengths. The radiated wavelengths can be adjusted by changing the operating temperature of the QCL source 202 providing the optical radiations in the near and mid infrared region of the electromagnetic spectrum, effectively covering the range of 0.2 µm to 20 µm. In addition, the power of the radiation emitted by the QCL source 202 may be tuned by tuning the operating conditions of the source. Optical radiation emitted by the QCL source 202 enters an air chamber 204 from a first end 204a, experiences multiple reflections inside the chamber (e.g., at a reflective surface 205) while traversing therethrough, and is received by a photodetector 206 located at a second end 204b of the chamber opposite the first end 204a. An optical path of the of the optical radiation through the chamber 204 is represented in FIG. 1B by an arrow 207. The optical radiation, or light, incident on the photodetector 206 generates a current, which is amplified and converted to a voltage by a transimpedance amplifier ("TIA") stage 208. The voltage is then digitized by an analog-to-digital converter ("ADC") 210 and the resulting digital data is processed by a controller 212. It will be noted that, as represented in FIG. 1B, multiple photodetectors, each with a corresponding TIA stage, may be deployed as deemed advantageous for implementing various embodiments.

The spectrometer system 200 must be able to measure the optical transmission of the gas sample over a range of frequencies sufficient to uniquely determine the concentration of acetone in the gas. The construction details of the QCL source 202 are chosen in order meet the frequency range requirements. The QCL 202 is constructed with a series of quantum wells. The physical size of the wells determines the nominal frequency of the emitted light, with each well enabling a narrow frequency band of light to be transmitted. The well that is activated can be controlled, thereby enabling the output frequency of the QCL 202 to be selected. Additionally, the frequency of the emitted light varies with temperature; accurately varying the temperature of the QCL enables the frequency to be continuously swept across different frequencies ranging from NIR to mid infrared ("MIR") range. The combination of frequencies selected and the frequency sweeps allow enough of the frequency band to be scanned to measure the concentration of acetone in the gas.

On the optical receiver side, the photodetector 206 and optical filter combination has a relatively uniform bandwidth over the transmitted light frequencies, with any variations therein being removed using a calibration routine. As a result, the photodetector 206 has minimal impact on the overall frequency transfer of the system 200. To reduce the power consumption of the laser 202 and remove the low frequency noise of the TIA and the ADC, a synchronous demodulation technique is used for the optical signal measurement. This technique involves pulsing the laser 202 and synchronously sampling the response at the output of the TIA 208. The pulse width of the laser 202 is selected based on the settling time requirements of the TIA 208 stage, with a typical pulse width being approximately 1 µs. The pulse, or modulation, rate of the laser 202 involves a tradeoff between the 1/f frequency of the TIA 208 and the sample rate of the ADC 210. The modulation rate of the laser 202 should be above the 1/f frequency to reduce the impact of the electrical noise, but low enough to avoid the use of a higher power, costlier ADC and impose additional processing burden on the controller 212. A typical modulation frequency may be approximately 10 KHz. The ADC 210 will normally sample the waveform at 4 times the modulation frequency to use IQ sampling, which improves the accuracy of the measurement.

In certain embodiments, auxiliary sensors can be used to improve the calibration of the measurement. For example, a temperature, pressure or humidity sensor 216, may be optionally employed inside the chamber 204 to measure air temperature and pressure within the chamber. The temperature, humidity and pressure can be used separately or in tandem in the calibration routine performed in the cloud. Additionally, an electrochemical sensor 218, may be optionally employed inside the chamber 204 to measure the target analyte or other gases inside the air chamber. The analyte measurement obtained from the electrochemical sensor can be used separately or in tandem in the calibration routine performed in the cloud. Because the system 200 is designed to be portable, it includes a battery 220 and power management functionality ("PMT") 222 as well.

Figure 2A:
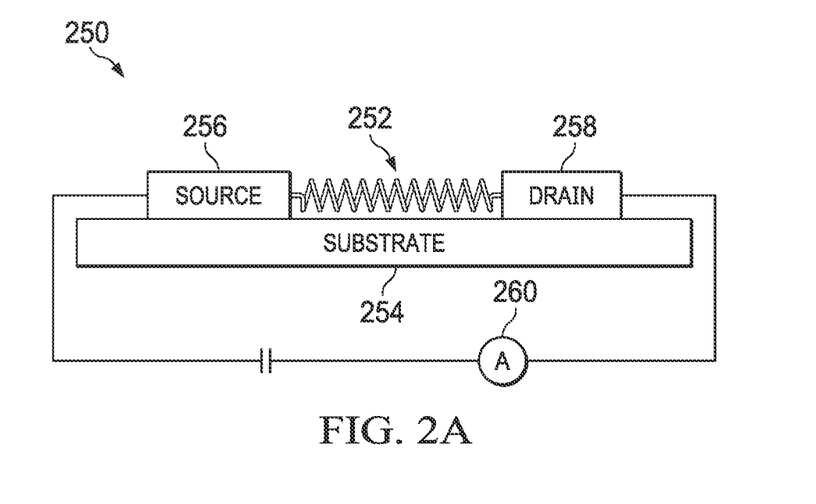
FIGS. 2A-2D illustrate various embodiments of an electrochemical sensor for use in a cloud-based portable miniaturized system for non-invasive real-time blood glucose analysis in accordance with embodiments described herein.
Figure 2B:
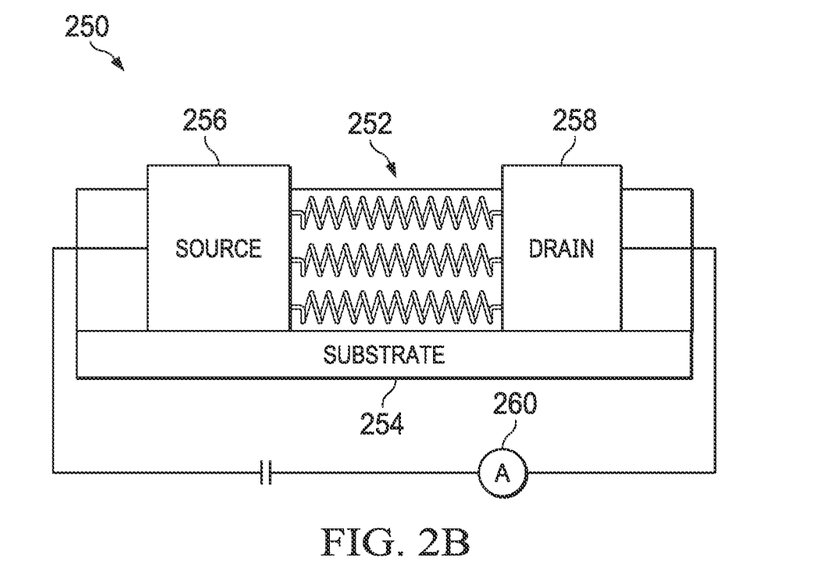
Figure 2C:
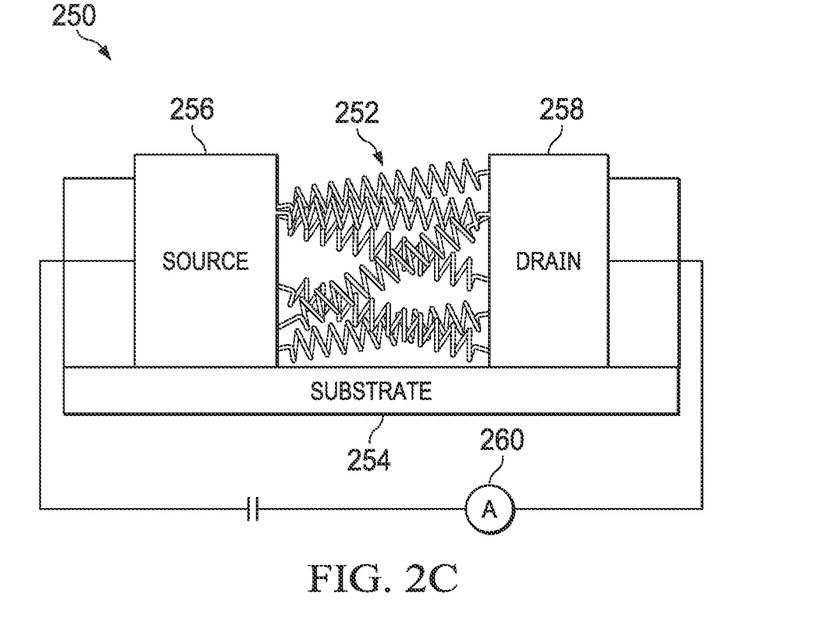
Figure 2D:
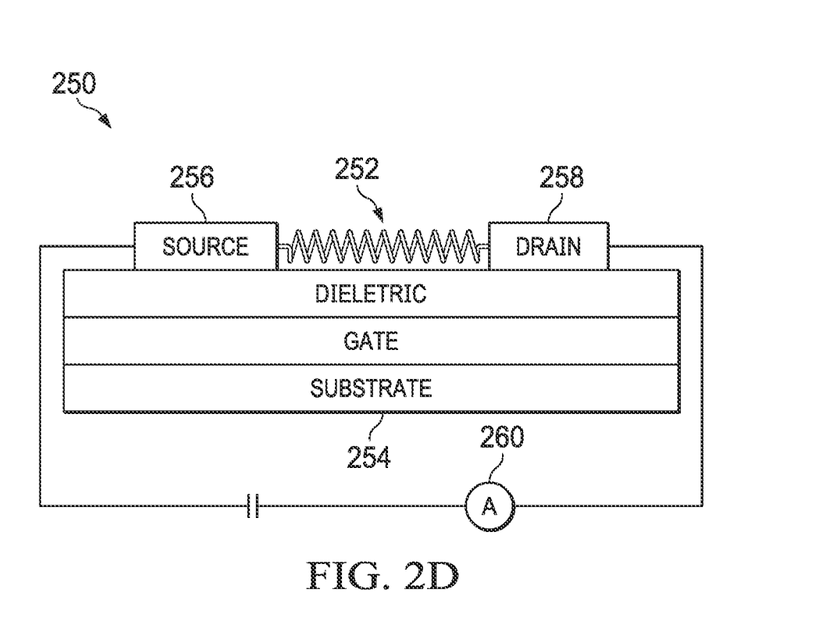

Example embodiments for implementing an electrochemical sensor, such as the electrochemical sensor 218 are further described below and illustrated in FIGS. 2A-2D. As shown in FIGS. 2A-2D, an electrochemical sensor 250 includes a sensing element 252, which may be fabricated from aligned single-wall or multi-wall carbon nanotubes ("CNTs") (as represented in FIG. 2B), randomly oriented single-wall or multi-wall CNTs (as represented in FIG. 2C), silicon nanowires, or metal nanowires. Sensing elements may be functionalized with proper chemistry, such as antibodies, aptamers, enzymes, and/or doping elements, such as copper, etc., to capture and target desired analytes, such as acetone, ethylene, or other volatile organic carbons ("VOCs"). This also provides the desired specificity to the system. The sensor 250 could be constructed as a two-terminal device, as illustrated in FIGS. 2A-2C, or a three-terminal device, such as a top-gated or a back-gated field effect transistor ("FET"), as illustrated in FIG. 2D. A substrate 254 of the sensor 250 may be a flexible substrate, such as polyethylene terephthalate ("PET"), or a rigid substrate, such as silicon.

In operation, the sampled air/breath is passed on top of the electrochemical sensor 250, where the targeted analytes/molecules are captured by the functionalized chemistry present on top of the sensing elements 252. This capture of target molecules will result in change in the resistivity of a channel between a source 256 and a drain 258 or the two terminals, which results in a change in current measured by an ammeter 260. The change in current is correlated to the amount of target molecules/analytes, which is decoded by the chemometric algorithms analyzing the data. The air or breath sampled in the sampling chamber is analyzed with both the optical sensing system and with the embedded electrochemical system. Applications of the system include, but are not limited to, breath analysis for blood glucose detection, capturing critical biomarkers from the breath for various severe illness such as lung cancer, cardiac problems, etc., detection of ethylene, which is a marker for fruit ripeness, and others, etc.

Referring again to FIG. 1B, in general, the functions of the controller 212 include synchronously triggering the light source and the ADC sampling, accumulating and compressing the ADC data, operating a thermoelectric cooler ("TEC") 224 to maintain the desired temperature, and communicating with a gateway 226 to transmit data and instructions to and from cloud services 228. The PMT 222 provides the required supply voltages for the electronics from the battery 220 or an externally supplied power source. The PMT 222 also recharges the battery from an externally supplied power source. The QCL 202 is a multi-wavelength laser that is excited from a high energy LED. The QCL down converts LED optical energy into an array of longer wavelengths, which are selected to align with the absorption wavelength of acetone.

The TEC 224 is provided to stabilize the temperature of the QCL 202 (via a thermal connection 225) as necessary to calibrate and stabilize the QCL operation. The gateway 226 provides a communications link between the controller 212 and the cloud services 228. In one embodiment, the communications link includes a wireless connection, such as Bluetooth low energy ("BLE"), WIFI, or LTE Cat-M.

The cloud services infrastructure includes several elements, including a spectral database 230, a calibration unit 232, and a processing unit 234, which includes preprocessing algorithms, chemometric models, and lookup tables. In one embodiment, the spectral database is built using the described system and gas samples with known concentrations of acetone at various humidity and temperature conditions. It consists of optical transmission measurements of the acetone at the wavelengths of interest in near and mid infrared supported by the chip-scale QCL.

Figure 3A:
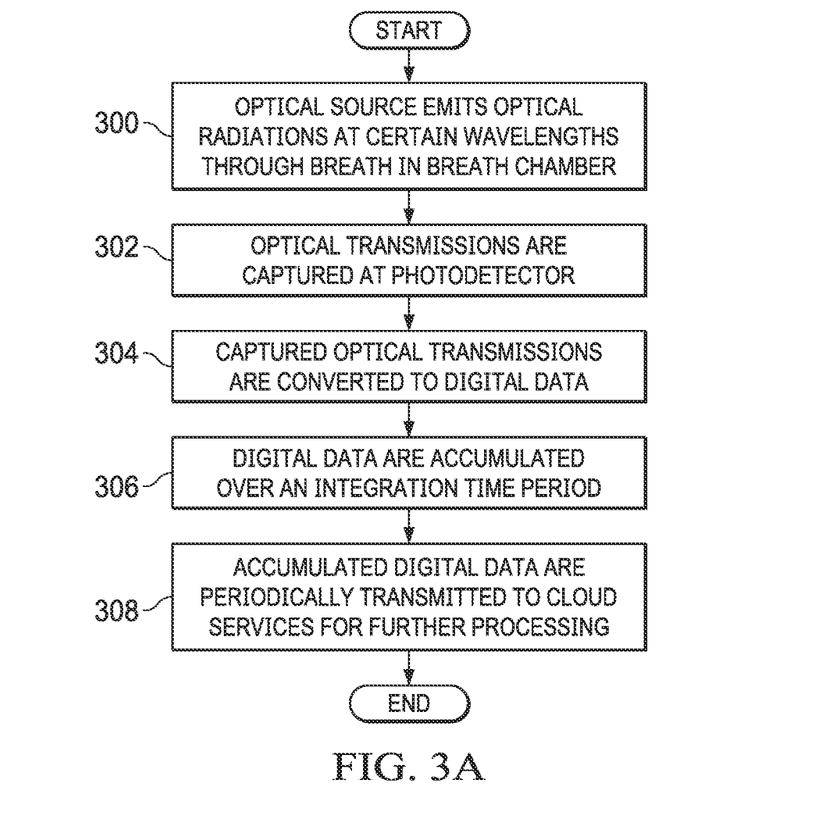
FIGS. 3A and 3B are flowcharts illustrating operation of a cloud-based portable miniaturized system for non-invasive real-time blood glucose analysis in accordance with embodiments described herein.
Figure 3B:
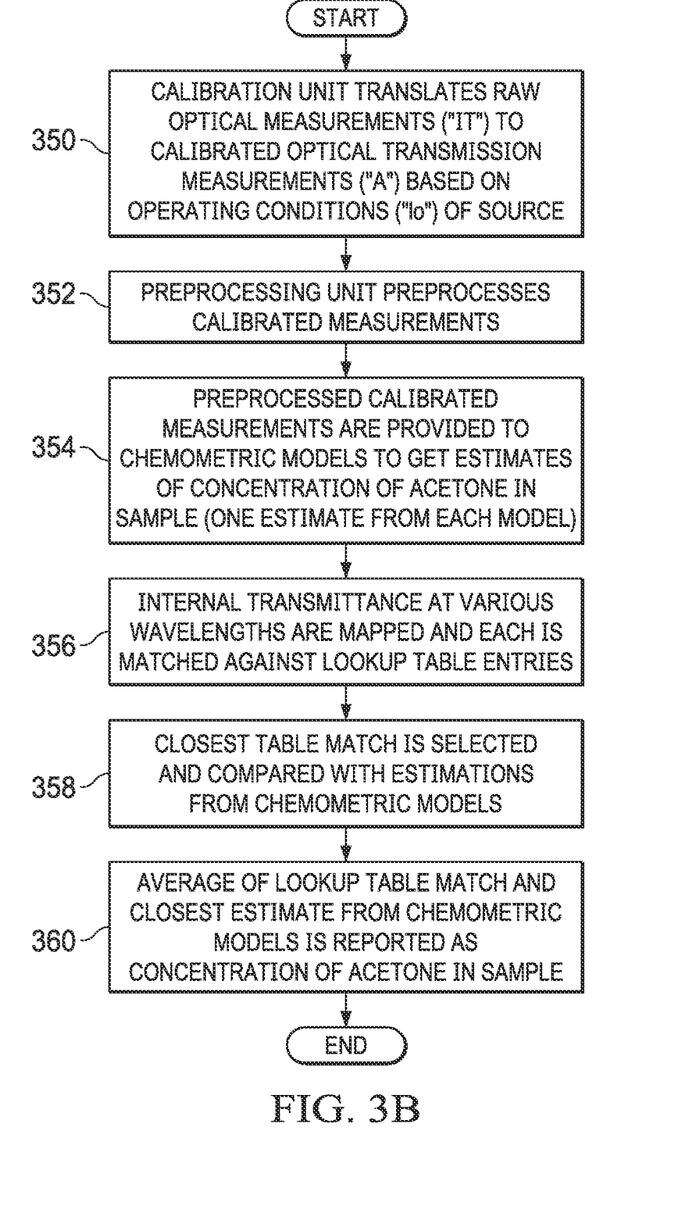

FIGS. 3A and 3B are flowcharts illustrating operation of a cloud-based portable miniaturized system for non-invasive real-time blood glucose analysis in accordance with embodiments described herein. Referring to FIG. 3A, in step 300, an optical source, such as a QCL, emits a laser beam comprising highly focused optical radiations at certain wavelengths through air (e.g., breath) contained in an air chamber. In step 302, the resulting optical transmissions are captured at a photodetector and converted into digital data in step 304. In step 306, the digital data are accumulated over an integration time period and in step 308, the accumulated data are periodically transmitted to cloud services for further processing.

Referring now to FIG. 3B, in step 350, the calibration unit translates the raw optical measurements captured by the photodetector ("IT") to a calibrated optical transmission measurement ("A") based on the operating conditions ("Io") of the chip-scale QCL. The calibration unit basically generates the optical transmission based on the Beer-Lambert-Bouguer law defined as:

$$A = -\log 10(IT/Io)$$

where:
IT is the monochromatic radiant power transmitted by the absorbing medium;
Io is the monochromatic radiant power incident on the medium; and
τi is the internal transmittance (=IT/Io).

The processing unit consists of several processing blocks, such as preprocessing algorithms, chemometric models, and lookup tables. In step 352, preprocessing algorithms preprocess the calibrated transmission (i.e., the output of the calibration unit) and support various elements, such as log 10, In, first and second derivatives, averaging, Standard Normal Variate ("SNV"), autoscaling, baseline correction, and Multiplicative Scatter Correction ("MSC"), for example. Chemometric models include at least three such models based on Multiple Linear Regression ("MLR") and Principal Components Regression ("PCR"), and Partial Least Square ("PLS") regression. Lookup tables include internal transmittance ("τi") at various wavelengths for different concentrations of the acetone. The look-up table is constructed along with the database using the samples of acetone in gas samples under various operating conditions such as humidity, temperature, and QCL source power ("Io") etc. Look-up tables are utilized as a mean to validate the estimates made by the chemometric models.

As previously noted, the raw optical measurements ("IT") measured at the photodetector are calibrated by the calibration unit to generate the internal transmittance ("τi") at the various supported NIR and MIR wavelengths. These calibrated measurements are preprocessed and in step 354, the measurements are provided to the three chemometric models to estimate the concentration of acetone in the sample, with each model providing one estimate. The preprocessing scheme, comprising a combination of preprocessing algorithms, is fixed for a given chemometric model. In addition, in step 356, the internal transmittance ("τi") measured at various wavelengths is mapped and matched against lookup table entries. In step 358, the estimated concentration that provide the closest match to the lookup table entry is then picked and compared to the estimations from the chemometric model. The average of look-up table match and the closest estimate of it from the chemometric models is then reported back to the user as the measured acetone concentration in step 360.

Figure 4:
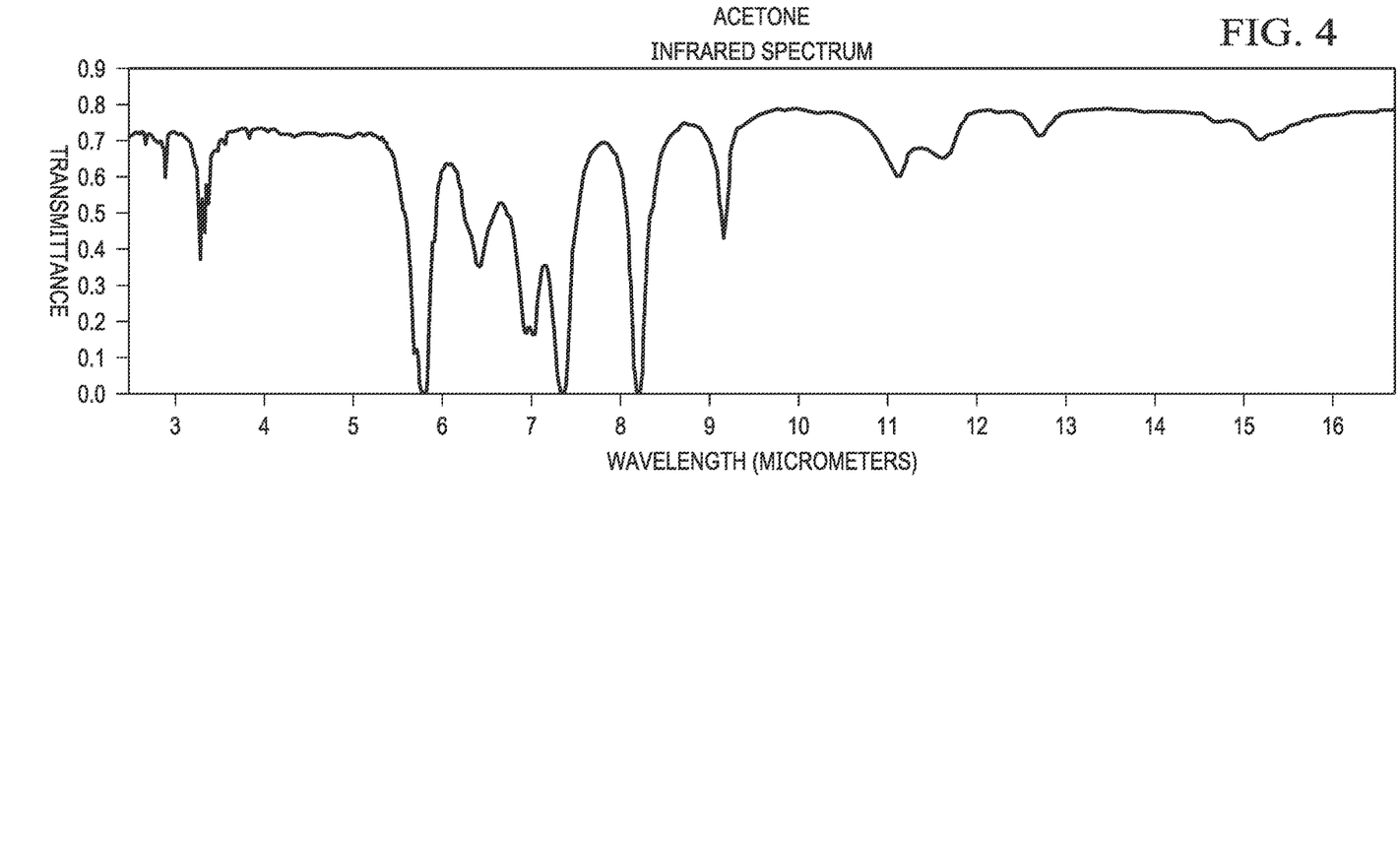
FIG. 4 is a graph illustrating the respective IR spectra of acetone that may be detected using a cloud-based portable miniaturized system for non-invasive real-time blood glucose analysis in accordance with embodiments described herein.

FIG. 4 is a graph illustrating the IR spectrum acetone. The described system targets the spectral signatures of acetone available in the region of 5 μm-10 μm. Table I below summarizes concentrations of acetone in a healthy vs. a diabetic individual.

TABLE 1

| Attribute | Healthy | Type 1 Diabetic | Type 2 Diabetic |
| --- | --- | --- | --- |
| Percent of total Acetone produced that is excreted through Urine and Breath | 2-30% | Up to ~52% | NA (More research needed) |
| Concentration Levels in Exhaled Breath | 300-900 ppb | In excess of 1800 ppbv | Of 25 T2D patients mean = 2.167 ppmv |
| 24-Hour Fasting | 177-2441 ppb | Increase to 5.66 ppm (+) | NA (more research needed) |

Historically, blood glucose has been measured by placing a drop of a patient's blood on an electrochemical strip sensor and inserting it into a sensor reader device that performs a voltammetry measurement to determine glucose levels. Embodiments described herein avoid the need to draw blood and thus provide a non-invasive means for determining a blood glucose level. Another historical method for monitoring blood glucose levels involves use of a continuous glucose monitor ("CGM"), which determines glucose levels on a continuous basis (e.g., every few minutes). A typical CGM system consists of a disposable glucose sensor placed just under the skin, which is worn for a few days until replacement, a link from the sensor to a non-implanted transmitter which communicates to a radio receiver, and an electronic receiver worn like a pager (or insulin pump) that displays glucose levels with nearly continuous updates, as well as monitors rising and falling trends. CGMs measure the concentration of glucose in a sample of interstitial fluid. As a result, CGMs suffer a variety of shortcomings, including that they must be calibrated with a traditional blood glucose measurement (using current technology) and therefore require both the CGM system and occasional "finger stick," and that glucose levels in interstitial fluid lag behind blood glucose values, such that patients are required to undergo traditional finger stick measurements for calibration (typically twice per day) and are often advised to use fingerstick measurements to confirm hypo- or hyperglycemia before taking corrective action.

Non-invasive glucose monitoring systems may use one or more of bioimpedance spectroscopy, electromagnetic sensing, fluorescence technology, mid-infrared spectroscopy, near infrared spectroscopy, optical coherence tomography, optical polarimetry, raman spectroscopy, reverse iontophoresis, and ultrasound technology to measure blood glucose non-invasively from the skin.

Embodiments described herein are a cloud-based portable handheld system for non-invasive real-time blood glucose analysis in which a tunable chip-scale QCL laser is used and emits different wavelengths by changing the temperature. Additionally, the fact that the system is small, handheld, and easily portable allows easy fixture of the system to the sampling medium. Still further, the system is cloud-based and provides algorithms for data processing offering real time blood glucose analysis.

In Example 1, a method for implementing a cloud-based portable miniaturized system for performing non-invasive blood glucose level measurement in real time may include translating raw optical measurement ("IT") to calibrated optical transmission measurements ("A") based on operating conditions ("Io") of an optical transmission source of the system; preprocessing the calibrated optical transmission measurements; providing the preprocessed calibrated optical transmission measurements to at least one chemometric model to obtain an estimate of a concentration of acetone in the breath; mapping internal transmittance at a first wavelength and matching the mapped internal transmittance to a lookup table entry; and reporting an average of the matched lookup table entry and the estimate from the at least one chemometric model as a concentration of the acetone in the breath.

In Example 2, the method of Example 1 may further include the translation being performed in accordance with $A = -\log 10(IT/Io)$.

In Example 3, the method of any of Examples 1-2 may further include the first wavelength aligning with an absorption wavelength of a particular concentration of acetone.

In Example 4, a method for implementing a cloud-based portable miniaturized system for performing non-invasive blood glucose level measurement in real time may include using an optical source to emit optical radiations at certain wavelengths through breath in an air collection chamber; receiving the emitted optical transmissions at a photodetector; converting the received optical transmissions to digital data; accumulating the digital data for a first time period; and periodically transmitting the accumulated digital data to a cloud service for further processing.

In Example 5, the method of Example 4 may further include the optical source comprising a Quantum Cascade Laser ("QCL").

In Example 6, the method of any of Examples 4-5 may further include the optical source comprising at least one of a miniaturized near infrared ("NIR") spectrometer and a plurality of discrete LEDs.

In Example 7, the method of any of Examples 4-6 may further include adjusting an optical path length between the source and the detector by adjusting a number of reflections experienced by the optical radiations.

In Example 8, the method of any of Examples 4-7 may further include each of the certain wavelengths aligning with an absorption wavelength of a particular concentration of acetone.

In Example 9 an apparatus for implementing a cloud-based portable miniaturized system for performing non-invasive blood glucose level measurement in real time may include a system housing for collecting breath of a user, the system housing comprising a spectrometer printed circuit board ('PCB') connected to the inlet diaphragm; and a reflective surface opposite the spectrometer PCB, wherein an air containment section is disposed between the spectrometer PCB and the reflective surface. The apparatus of Example 9 may further include an optical source disposed on a surface of the spectrometer PCB, wherein radiation emitted from the optical source travels through breath disposed within the air containment section, is reflected by the reflective surface, and is detected by the optical detector.

In Example 10, the apparatus of Example 9 may further include the system housing further comprising a mouthpiece for receiving breath expelled by the user.

In Example 11, the apparatus of any of Examples 9-10 may further include the system housing further comprises a particulate filter for filtering particulates from the received breath.

In Example 12, the apparatus of any of Examples 9-11 may further include an inlet diaphragm connected to the particulate filter.

In Example 13, the apparatus of any of Examples 9-12 may further include an outlet diaphragm connected to the air containment tube.

In Example 14, the apparatus of any of Examples 9-13 may further include a reflective coating disposed on an inside of each of the air containment section to adjust an optical path of the radiation through the breath disposed within the air containment section.

In Example 15, the apparatus of any of Examples 9-14 may further include the optical source comprising a Quantum Cascade Laser ("QCL").

In Example 16, the apparatus of any of Examples 9-15 may further include the optical source comprising at least one of a miniaturized near infrared ("NIR") spectrometer and a plurality of discrete LEDs.

In Example 17, the apparatus of any of Examples 9-16 may further include a sensor for measuring a temperature of the breath disposed within the breath collections section.

In Example 18, the apparatus of any of Examples 9-17 may further comprise electronics for converting the detected radiation into digital data and calculating a raw spectral power density of the detected radiation.

In Example 19, the apparatus of any of Examples 9-18 may further include a gateway device for transmitting the digital data and the raw spectral power density to a cloud service for processing.

In Example 20, the apparatus of any of Examples 9-19 may further include the optical source emitting optical radiations at certain wavelengths through breath in the air collection chamber.

In Example 21, the apparatus of any of Examples 9-20 may further include each of the certain wavelengths aligning with an absorption wavelength of a particular concentration of acetone.

In Example 22, an apparatus for implementing a cloud-based portable miniaturized system for performing non-invasive blood glucose level measurement in real time may comprise a system housing for collecting breath of a user, the system housing comprising a mouthpiece for receiving breath expelled by the user; a particulate filter for filtering particulates from the received breath; an inlet diaphragm connected to the particulate filter; a spectrometer printed circuit board ('PCB') connected to the inlet diaphragm a reflective surface opposite the spectrometer PCB; and an outlet diaphragm connected to the outlet diaphragm, wherein an air containment section is disposed between the spectrometer PCB and the reflective surface. The apparatus may further include an optical source disposed on a surface of the spectrometer PCB, wherein radiation emitted from the optical source travels through breath disposed within the air containment section, is reflected by the reflective surface, and is detected by the optical detector.

In Example 23, the apparatus of Example 22 may further include a reflective coating disposed on an inside of each of the air containment section to adjust an optical path of the radiation through the breath disposed within the air containment section.

In Example 24, the apparatus of any of Examples 22-23 may further include the optical source comprising a Quantum Cascade Laser ("QCL").

In Example 25, the apparatus of any of Examples 22-24 may further include the optical source comprising at least one of a miniaturized near infrared ("NIR") spectrometer and a plurality of discrete LEDs.

In Example 26, the apparatus of any of Examples 22-25 may further include a sensor for measuring a temperature of the breath disposed within the breath collections section.

In Example 27, the apparatus of any of Examples 22-26 may further include electronics for converting the detected radiation into digital data and calculating a raw spectral power density of the detected radiation.

In Example 28, the apparatus of any of Examples 22-27 may further include a gateway device for transmitting the digital data and the raw spectral power density to a cloud service for processing.

In Example 29, the apparatus of any of Examples 22-28 may further include the optical source emitting optical radiations at certain wavelengths through breath in the air collection chamber.

In Example 30, the apparatus of any of Examples 22-29 ay further include each of the certain wavelengths aligning with an absorption wavelength of a particular concentration of acetone.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The 'means for' in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying FIGURES (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the FIGURES. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the FIGURES in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method for performing a non-invasive blood glucose level measurement, comprising:
    translating raw optical measurements ("IT") to calibrated optical transmission measurements ("A") based on operating conditions of a light source device external to a body of a subject, with a ratio of the raw optical measurements and the operating conditions defining an internal transmittance, the operating conditions comprising radiant power ("Io") of optical radiation emitted by the light source device;
    preprocessing the calibrated optical transmission measurements;
    providing the preprocessed calibrated optical transmission measurements to at least one chemometric model to obtain respective estimates of a concentration of acetone in a breath of the subject;
    determining, using a lookup table, a defined internal transmittance value corresponding to the internal transmittance measured at a first wavelength;
    determining, using the lookup table and the defined internal transmittance value, a defined concentration of acetone;
    selecting, from the respective estimates, a particular estimate of the concentration of acetone in the breath of the subject that is closest to the defined concentration of acetone;
    reporting an average of the defined concentration of acetone and the particular estimate as a measured concentration of the acetone in the breath of the subject, with the measured concentration of the acetone in the breath representing a level of blood glucose in the subject.

2. The method of claim 1, wherein the translating the raw optical measurements to the calibrated optical transmission measurements is performed in accordance with $A = -\log_{10}(I_T/I_o)$.

3. The method of claim 1, wherein the first wavelength aligns with an absorption wavelength of a particular concentration of acetone.

4. The method of claim 1, wherein the lookup table comprises first values of the internal transmittance at respective wavelengths for a first concentration of acetone and second values of internal transmittance at respective wavelengths for a second concentration of acetone.

* * * * *